(12) United States Patent
Kim et al.

(10) Patent No.: US 9,260,717 B2
(45) Date of Patent: Feb. 16, 2016

(54) METHOD OF SCREENING FOR CHAPERONIN MODULATOR

(75) Inventors: Kyong Tai Kim, Pohang-si (KR); Sangjune Kim, Gwangju (KR)

(73) Assignee: POSTECH ACADEMY-INDUSTRY FOUNDATION, Pohang-Si (KR)

( * ) Notice: Subject to any disclaimer, the term of this patent is extended or adjusted under 35 U.S.C. 154(b) by 0 days.

(21) Appl. No.: 14/115,730

(22) PCT Filed: Aug. 20, 2012

(86) PCT No.: PCT/KR2012/006602
§ 371 (c)(1),
(2), (4) Date: Nov. 5, 2013

(87) PCT Pub. No.: WO2013/027986
PCT Pub. Date: Feb. 28, 2013

(65) Prior Publication Data
US 2014/0057967 A1    Feb. 27, 2014

(30) Foreign Application Priority Data

Aug. 24, 2011 (KR) .................. 10-2011-0084690

(51) Int. Cl.
| | |
|---|---|
| *G01N 33/15* | (2006.01) |
| *A61P 25/28* | (2006.01) |
| *C12N 15/113* | (2010.01) |
| *C12Q 1/48* | (2006.01) |
| *C12Q 1/68* | (2006.01) |
| *G01N 33/573* | (2006.01) |
| *A61K 31/713* | (2006.01) |

(52) U.S. Cl.
CPC .......... *C12N 15/1137* (2013.01); *A61K 31/713* (2013.01); *C12Q 1/485* (2013.01); *C12Q 1/6809* (2013.01); *G01N 33/573* (2013.01); *G01N 2500/02* (2013.01); *G01N 2500/04* (2013.01)

(58) Field of Classification Search
USPC ............. 424/9, 9.1; 435/6.1, 6.11, 6.12, 6.13, 435/7.4, 91.1, 91.3, 375; 530/300, 350; 536/23.1, 24.5; 514/1, 2, 44
See application file for complete search history.

(56) References Cited

U.S. PATENT DOCUMENTS

2012/0165403 A1* 6/2012 Gasiewicz et al. ............ 514/456

FOREIGN PATENT DOCUMENTS

| CN | 1177351 | 3/1998 |
|---|---|---|
| CN | 102083804 | 6/2011 |
| EP | 1289512 | 3/2003 |
| JP | 2003-535829 | 12/2003 |
| WO | 01/32694 | 5/2001 |
| WO | 2004/045543 | 6/2004 |
| WO | 2005/116082 | 12/2005 |

OTHER PUBLICATIONS

Dorland's Medical Dictionary, chaperonin—definition of chaperonin by Medical dictionary (2012).*
Choi et al, Poster: Accumulation of polyglutamine aggregates by vaccinia-related kinase 2 (VRK2), Jul. 14, 2008, Federation of European Neurosciences Societies (FENS) Conference, FENS Abstr., vol. 4.*
Kim et al, J. Neurochem., vol. 110, pp. 190-191 (Sep. 2009).*
H.W. Kim, et al., "Increased Expression of Apoptotic Factors in Postmortem Brain from Bipolar Disorder Patients", International Society for Neurochemistry, 110 (Suppl. 2) , pp. 167-210, (See pp. 189-190.) (Jul. 2009).
Aisllinn J. Williams, et al., "Polyglutamine neurodegeneration: protein misfolding revisited", Trends in Neurosciences, vol. 31, No. 10, (See Abstract; pp. 524-525.) (Sep. 6, 2008).
Chunling Yi, et al., "Affinity purification reveals the association of WD40 protein constitutive photomorphogenic 1 with the hetero-oligomeric TCP-1 chaperonin complex in mammalian cells", The Interntional Journal of Biochemistry & Cell Biology. (See the whole document)(Feb. 2006).
Kim, S., et al.: "Accumulation of polyglutamine aggregates by vaccinia-related kinase 2 (VRK2) via negative regulation of chaperonin TRiC", Journal of Neurochemistry, vol. 110, Sep. 30, 2009, pp. 190-191.
Choi Y H et al.: "FENS Forum 2008", Jan. 1, 2008, p. 82, XP055172639.
Do-Young Park, et al."Vaccinia-related kinase 2 (VRK2), negative regulator of chaperonin TRiC/CCT", May 27, 2007, XP002736637.
Stephen Tam et al.: "The chaperonin TRiC blocks a huntigtin sequence element that promotes the conformational switch to aggregation", Nature Structural & Molecular Biology, vol. 16, No. 12, Nov. 15, 2009, pp. 1279-1285, XP055173031.

(Continued)

Primary Examiner — Jane Zara
(74) Attorney, Agent, or Firm — Lex IP Meister, PLLC

(57) ABSTRACT

The present invention relates to a method of screening for modulator of chaperonin that is involved in protein aggregation inducing neurodegenerative diseases such as Alzheimer's disease, Parkinson's disease and Huntington's disease, use of the chaperonin modulator screened by the method for prevention and treatment of neurodegenerative diseases. According to the present invention, novel negative chaperonin modulator is provided, and chaperonin modulator may be more rapidly and conveniently screened with the negative modulator as a target. Furthermore, by using the screened material, neurodegenerative diseases such as Alzheimer's disease, Parkinson's disease and Huntington's disease may be effectively prevented or treated without concern for cell death due to autophagy, which is the existing method of removing protein aggregate.

3 Claims, 9 Drawing Sheets

(56) References Cited

OTHER PUBLICATIONS

S. Kim et al.: "Vaccinia-Related Kinase 2 Mediates Accumulation of Polyglutamine Aggregates via Negative Regulation of the Chaperonin TRiC", Molecular and Cellular Biology, vol. 34, No. 4, Dec. 2, 2013, pp. 643-652, XP055173035.

Chinese Patent Office, Search Report dated Jan. 27, 2015, which was attached to the Office Action dated Feb. 2, 2015, of the corresponding Chinese Patent Application No. 201280040109.7.

European Patent Office, extended European Search Report dated Mar. 25, 2015, of the corresponding European Patent Application No. 12826437.1.

Kim S. et al., TH06-42, "Accumulation of Polyglutamine Aggregates by Vaccinia-Related Kinase 2(VRK2) Via Negative Regulation of Chaperonin TRiC" Journal of Neurochemistry, vol. 110, No. suppl.2, pp. 190-191, Sep. 2009.

Choi Y. H. et al., "Accumulation of polyglutamine aggregates by vaccinia-related kinase 2(VRK2)", FENS Forum 2008, vol. 4, 082.8, Jul. 14, 2008, [online] http://www.ncbi.nlm.nih.gov/pmc/articles/PMC2788664/pdf/nihms145408.pdf.

Stephen Tam et al., "The Chaperonin TRIC Blocks a Huntingtin Sequence Element that promotes the Conformational Switch to Aggregation", Nat Struct Mol Biol., Dec. 2009, vol. 16, No. 12, pp. 1279-1285, doi:10.1038/nsmb.1700. [online] http://www.ncbi.nlm.nih.gov/pmc/articles/PMC2788664/pdf/nihms145408.pdf(available in PMC 2010).

Yi C. et al., "Affinity purification reveals the association of WD40 protein constitutive photomorphogenic 1 with the hetero-oligomeric TCP-1 chaperonin complex in mammalian cells", Int J Biochem Cell Biol., vol. 38, No. 7, pp. 1076-1083, Feb. 8, 2006.

Journal of neurochemistry, "Thursday Poster Session TH01 Brain monoamine system", Jul. 29, 2009, p. 167-210.

* cited by examiner mRNA level

```
                          SEQUENCE LISTING

<160> NUMBER OF SEQ ID NOS: 12

<210> SEQ ID NO 1
<211> LENGTH: 21
<212> TYPE: RNA
<213> ORGANISM: Artificial Sequence
<220> FEATURE:
<223> OTHER INFORMATION: siVRK2

<400> SEQUENCE: 1
gcaagguucu ggaugauauu u                                              21

<210> SEQ ID NO 2
<211> LENGTH: 19
<212> TYPE: RNA
<213> ORGANISM: Artificial Sequence
<220> FEATURE:
<223> OTHER INFORMATION: siCOP1

<400> SEQUENCE: 2
gaaaugaccu gcaauucga                                                 19

<210> SEQ ID NO 3
<211> LENGTH: 22
<212> TYPE: RNA
<213> ORGANISM: Artificial Sequence
<220> FEATURE:
<223> OTHER INFORMATION: siRBX1

<400> SEQUENCE: 3
gacuuucccu gcuguuaccu aa                                             22

<210> SEQ ID NO 4
<211> LENGTH: 29
<212> TYPE: DNA
<213> ORGANISM: Artificial Sequence
<220> FEATURE:
<223> OTHER INFORMATION: forward primer of VRK2

<400> SEQUENCE: 4
acgcgtcgac atgccaccaa aaagaaatg                                      29

<210> SEQ ID NO 5
<211> LENGTH: 26
<212> TYPE: DNA
<213> ORGANISM: Artificial Sequence
<220> FEATURE:
<223> OTHER INFORMATION: reverse primer of VRK2

<400> SEQUENCE: 5
aaggatcctc agagaaaaaa taaagc                                         26

<210> SEQ ID NO 6
<211> LENGTH: 33
<212> TYPE: DNA
<213> ORGANISM: Artificial Sequence
<220> FEATURE:
<223> OTHER INFORMATION: forward primer of K61A

<400> SEQUENCE: 6
gcaagacatg tagtagcagt ggaatatcaa gaa                                 33
```

```
<210> SEQ ID NO 7
<211> LENGTH: 33
<212> TYPE: DNA
<213> ORGANISM: Artificial Sequence
<220> FEATURE:
<223> OTHER INFORMATION: reverse primer of K61A

<400> SEQUENCE: 7
ttcttgatat tccactgcta ctacatgtct tgc                                    33

<210> SEQ ID NO 8
<211> LENGTH: 42
<212> TYPE: DNA
<213> ORGANISM: Artificial Sequence
<220> FEATURE:
<223> OTHER INFORMATION: HA epitope

<400> SEQUENCE: 8
atggcctcct acccttatga tgtgccagat tatgcctctc cc                          42

<210> SEQ ID NO 9
<211> LENGTH: 30
<212> TYPE: DNA
<213> ORGANISM: Artificial Sequence
<220> FEATURE:
<223> OTHER INFORMATION: forward primer of VRK2 RT

<400> SEQUENCE: 9
tttagcatat gatgaaaagc caaactatca                                        30

<210> SEQ ID NO 10
<211> LENGTH: 30
<212> TYPE: DNA
<213> ORGANISM: Artificial Sequence
<220> FEATURE:
<223> OTHER INFORMATION: reverse primer of VRK2 RT

<400> SEQUENCE: 10
tgagactctt gatatttctg tcttctcctt                                        30

<210> SEQ ID NO 11
<211> LENGTH: 30
<212> TYPE: DNA
<213> ORGANISM: Artificial Sequence
<220> FEATURE:
<223> OTHER INFORMATION: forward primer of GAPDH RT

<400> SEQUENCE: 11
ctttggtatc gtggaaggac tcatgaccac                                        30

<210> SEQ ID NO 12
<211> LENGTH: 30
<212> TYPE: DNA
<213> ORGANISM: Artificial Sequence
<220> FEATURE:
<223> OTHER INFORMATION: reverse primer of GAPDH RT

<400> SEQUENCE: 12
ccaccactga cacgttggca gtggggacac                                        30
```

METHOD OF SCREENING FOR CHAPERONIN MODULATOR

FIELD OF THE INVENTION

The present invention relates to a method of screening for modulator of chaperonin that is involved in protein aggregation inducing neurodegenerative diseases such as Alzheimer's disease, Parkinson's disease and Huntington's disease, and use of the chaperonin modulator screened thereby for prevention and treatment of neurodegenerative diseases.

BACKGROUND OF THE INVENTION

Representative symptoms of neurodegenerative diseases such as Alzheimer's disease, Parkinson's disease and Huntington's disease include aggregation of specific protein. Protein aggregate suppresses action of proteasome which is a protein decomposition device in cells, and inhibits transfer of transport protein. And, it is aggregated together with other transcription factors and isolates them to change gene transcription. Furthermore, it disturbs the action of mitochondria, thereby inducing oxidative stress to induce cell death. Particularly, it may cause side effects of neural signal transduction through synapse due to the above actions, and it may induce neuronal death to cause declination of brain function.

Recently, many of neurodegenerative disease studies have focused on removing already formed aggregates using autophagy. There is a study result suggesting specific removal of protein aggregates. However, the autophagy is known to gain energy by decomposing its cell organelles when there is energy imbalance in the cells, and if the control is not properly achieved, cell death may be caused by autophagy.

DISCLOSURE

Technical Problem

Accordingly, it is an object of the present invention to provide a method for screening novel modulator that controls the action of chaperone for maintaining correct protein folding by inhibiting initiation of protein aggregation.

Solution to Problem

As the result of studies, the inventors identified that vaccinia-related kinase 2 (VRK2) is related to the amount and/or stability of chaperonin protein, one of molecular chaperone, and specifically found out that the VRK2 degrades chaperonin depending on enzyme activity. In the degradation process of chaperonin, ubiquitin ligase COP1 complex interacts with the VRK2. Therefore, it was confirmed that the two substances may act as an important target for screening chaperonin modulator, and the present invention was completed. The screened chaperonin modulator may be an effective active ingredient for prevention or treatment of neurodegenerative diseases.

Accordingly, one embodiment of the invention provides a method of screening for chaperonin modulator comprising 1) preparing candidate material and VRK2; 2) measuring the expression amount or kinase activity of VRK2; and 3) treating the VRK2 with the candidate material and measuring changes in the expression amount or kinase activity of VRK2.

Preferably, the VRK2 may be those originated from all eukaryote including human, and for example, it may have amino acid sequence of accession number BAA19109. And, preferably, it may be encoded by nucleotide sequence of accession number AB000450.

Preferably, the chaperonin may be chaperonin TRiC/CCT, more preferably, CCT4 (accession number NM_009837).

The modulation of chaperonin may preferably increase or decrease the amount and/or stability of chaperonin protein.

The candidate material is not specifically limited, it may include all materials that may increase or decrease the expression amount and/or enzyme activity of VRK2, and preferably, it may be various synthetic or natural materials including polypeptide, polynucleotide (antisense RNA, siRNA, and the like), and compounds.

The VRK2 may be a wild type, or it may be properly modified to increase activity. For example, the modified VRK2 may be modified by a proper tag, wherein the tag may be GST, H is, Flag, EGFP, DsRed1, and the like, and preferably, GST may be tagged at N-terminal of VRK2.

In the case where the chaperonin modulator is the material that increases the amount or stability of chaperonin protein, the method may preferably further include, after the step 3), 4-1) identifying the candidate material as a material that increases the amount or stability of chaperonin protein if the expression amount or kinase activity of VRK2 has been decreased compared to untreated control.

The expression amount or kinase activity of the VRK2 may be measured by a method commonly used in the biological experiment without specific limitations. For example, the existence or degree of kinase activity may be confirmed by in vitro kinase assay, but not limited thereto.

The VRK2 corresponds to a negative chaperonin modulator, and it was confirmed by the following Example 1 that the negative modulation is based on the enzyme activity of VRK2. Thus, if the expression amount or enzyme activity of VRK2 when the candidate material is treated is decreased compared to the expression amount or enzyme activity before treatment, the treated candidate material may be judged as a material that increases the amount and/or stability of chaperonin protein.

The material that increases the amount and/or stability of chaperonin protein according to the above method may be preferably double stranded siVRK2 consisting of a single stranded siVRK2 (D-004684-06, Dharmacon) (SEQ ID NO: 1) and a complementary strand thereof.

To the contrary, in the case where the chaperonin modulator is the material that decreases the amount or stability of chaperonin protein, the method may preferably further include, after the step 3), 4-2) identifying the candidate material as a material that decreases the amount or stability of chaperonin protein if the expression amount or kinase activity of VRK2 has been increased compared to untreated controls.

Meanwhile, since the effect of VRK2 on chaperonin, i.e., the degradation of chaperonin, is performed by interaction with ubiquitin ligase COP1 complex, COP1 may also act as an important target for screening chaperonin modulator. And, since VRK2 especially interacts with RBX1, which is a component of COP1 complex, RBX may also be an important target.

Therefore, another embodiment of the present invention provides a method for screening chaperonin modulator comprising 1) preparing a candidate material and COP1; 2) measuring the expression amount or enzyme activity of COP1; and 3) treating the COP1 with the candidate material and measuring changes in the expression amount or enzyme activity of COP1.

Preferable chaperonin and regulation of chaperonin may be the same as explained above.

The candidate material is not specifically limited, it may include all materials that may increase or decrease the expression amount and/or enzyme activity of COP1, and preferably it may be various synthetic or natural material including polypeptide, polynucleotide (antisense RNA, siRNA, and the like), and compounds.

The COP1 may be a wild type, or it may be properly modified to increase activity. For example, the modified COP1 may be modified with a proper tag, wherein the tag may be GST, His, Flag, EGFP, DsRed1, and the like, and preferably GST may be tagged at N-terminal of COP1.

For example, the COP1 may have nucleotide sequence of accession number BC094728. And, the RBX1 may have nucleotide sequence of accession number AF140598.

In the case where the chaperonin modulator is the material that increases the amount or stability of chaperonin protein, the method may preferably further include, after the step 3), 4-1) identifying the candidate material as a material that increases the amount or stability of chaperonin protein if the expression amount or enzyme activity of COP1 has been decreased compared to untreated control.

Since the COP1 corresponds to negative chaperonin modulator like the above explained VRK2, if the expression amount or enzyme activity of COP1 is decreased compared to the expression amount or enzyme activity before treatment of the candidate material, the treated candidate material may be identified as a material that increases the amount and/or stability of chaperonin protein (Example 4).

The expression amount or enzyme activity (activity as E3 ligase) of the COP1 may be measured by a method commonly used in the art without specific limitations.

The material that increases the amount and/or stability of chaperonin protein according to the screening method of chaperonin modulator may be preferably one or more selected from the group consisting of double stranded siCOP1 consisting of a single stranded siCOP1 (D-007049-01, Dharmacon) (SEQ ID NO: 2) and a complementary strand thereof, and double stranded siRBX1 consisting of a single stranded siRBX1 (Dharmacon) (SEQ ID NO: 3) and a complementary strand thereof.

To the contrary, in the case where the chaperonin modulator is the material that decreases the amount or stability of the chaperonin modulator, the method may preferably further include, after the step 3), 4-2) identifying the candidate material as a material that decreases the amount or stability of chaperonin protein if the expression amount or enzyme activity of COP1 has been increased compared to untreated control.

Meanwhile, since the interaction between the VRK2 and COP1 may be achieved through binding between the VRK2 and COP1, yet another embodiment of the invention provides a method for screening chaperonin modulator, comprising 1) preparing a candidate material, VRK2, and COP1; 2) measuring binding between the VRK2 and COP1; and 3) treating the VRK2 and COP1 with the candidate material and measuring binding between the VRK2 and COP1.

The candidate material is not specifically limited, it may include any material that may be expected to inhibit or promote the interaction between VRK2 and COP1, and it may be preferably various synthetic or natural material including polypeptide, polynucleotide (antisense RNA, siRNA, and the like), and compounds.

In the case where the chaperonin modulator is the material that increases the amount or stability of chaperonin protein, the method may preferably further include, after step 3), 4) identifying the candidate material as a material that increases the amount or stability of chaperonin protein if the binding between the VRK2 and COP1 has been inhibited by treatment of the candidate material.

Since the chaperonin maintains correct folding of protein by inhibiting protein aggregation, for example abnormal aggregation of huntingtin protein, material that increases the amount and/or stability of the chaperonin protein may be useful for prevention or treatment of a neurodegenerative disease occurred by protein aggregation.

Accordingly, yet another embodiment of the invention provides a composition for preventing or treating a neurodegenerative disease comprising a modulator screened by the above screening method of chaperonin modulator, particularly a material that increases the amount or stability of chaperonin protein, as an active ingredient.

And, yet another embodiment of the invention provides a method for preventing or treating a neurodegenerative disease comprising screening a material that increases the amount and/or stability of chaperonin protein according to the above screening method; and administering the screened modulator in an effective amount to a subject in need of prevention or treatment of a neurodegenerative disease.

Preferably, the subject in need of prevention or treatment of a neurodegenerative disease may be a mammal including human.

The neurodegenerative disease may be Alzheimer's disease, Parkinson's disease, or Huntington's disease, preferably Huntington's disease, but not limited thereto.

The composition for preventing or treating a neurodegenerative disease may preferably include 0.0001 to 99.9 wt %, more preferably 0.001 to 50 wt % of the material that increases the amount or lifespan of chaperonin, based on the total weight of the composition.

Preferably, the composition and the method for preventing or treating a neurodegenerative disease may further include appropriate carrier, excipient and diluents, and the like, commonly used for preparation and administration of a pharmaceutical composition, be prepared into an appropriate dosage form according to the material, and be provided through an administration route suitable for each dosage form. The appropriate dosage form and administration route according to the kind of modulators may be easily selected by one of ordinary skilled person in the art.

The carrier, excipient and diluents may include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and the like.

The pharmaceutical composition may be administered by oral or parenteral route according to a common method, and for example, for oral administration, it may be used in the form of powder, granule, tablet, suspension, emulsion, syrup, and the like, and for parenteral administration, it may be administered by intravenous, intramuscular, subcutaneous injection, and the like, but all possible administration routes may be applied without limitation.

Preferable administration amount may be those suitable for the subject and/or treatment or prevention of a disease, and it may be controlled according to various factors including age, gender, general health state and body weight of the subject, the kind and severance of diseases, the kind of dosage forms, the kinds and contents of other ingredients contained in the composition, secretion rate of the composition, administration route and period, and the like, and it may appropriately selected by one of ordinary skilled person in the art.

Advantageous Effects

According to the present invention, a novel negative chaperonin modulator is provided, and chaperonin modulator may be more rapidly and conveniently screened with the negative modulator as a target. Furthermore, by using the screened material, neurodegenerative diseases such as Alzheimer's disease, Parkinson's disease, or Huntington's disease, and the like may be effectively prevented or treated without concern for cell death due to autophagy, which is the existing method for removing protein aggregate.

MODE FOR INVENTION

Hereinafter, the present invention will be explained in detail with reference to preferable examples. However, the following examples are only to illustrate the invention, and the scope of the invention is not limited thereto.

Example 1

Experiment of Huntingtin Protein Aggregation Induction 1.1. Experiment of Huntingtin Protein Aggregation Induction in HEK293T Cell Line 1) Experiment Method To confirm if VRK2 may control protein aggregation, which is a major symptom of neurodegenerative diseases, huntingtin protein was overexpressed alone or together with VRK1 (the same protein kinase family as VRK2, AB000449) or VRK2 (AB000450) in human embryonic kidney cell line HEK293T (Korean Cell Line Bank) to measure the effect on the aspect of aggregation and huntingtin protein aggregation.

A polyglutamine tract exists in exon1 of huntingtin gene, and in this experiment, a clone having 103 glutamines was used so as to easily induce aggregation. The degree of symptoms of Huntington's disease and the time of onset of disease are related to the number of glutamines in the polyglutamine tract of the huntingtin gene exon1, particularly, when the number is equal or less than 25, it is referred to as a wild type, and when the number is equal or greater than 25, it is referred to as a mutant type, and it is observed that as the number of glutamines increases, the degree of the symptoms worsens and the time of onset of disease is advanced.

Figure 1A:
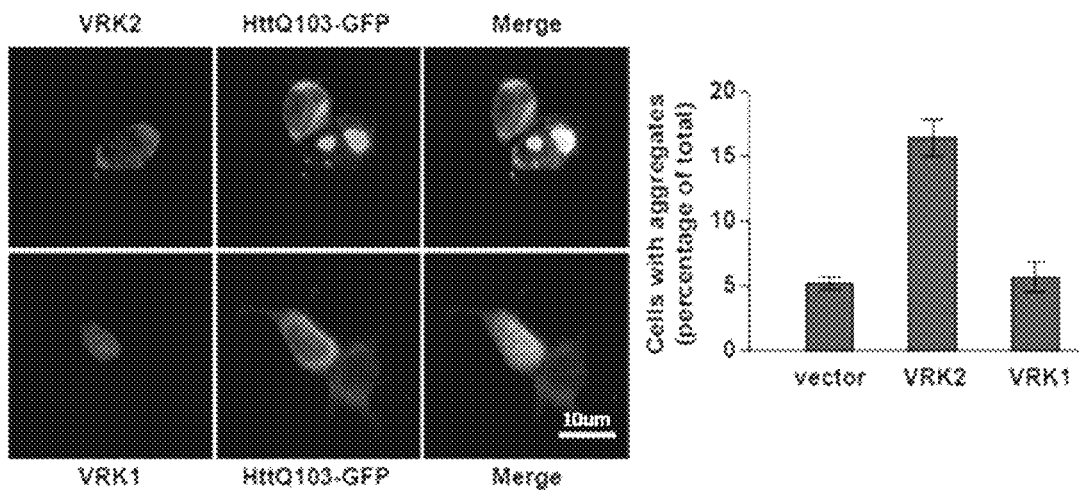
FIG. 1a to FIG. 1c show the results of measuring the effect of VRK2 on the huntingtin protein aggregation and aspect of huntingtin protein aggregation induction according to Example 1.

Specifically, using transfection reagent METAFECTENE (Biontex) according to the recommended amount of the manufacturer, huntingtin (Htt) protein gene expression vector of Htt-exon1-GFP-pcDNA3.1 vector (HTTQ103-GFP-pcDNA3.1) (obtained from Judith Frydman, Stanford university, CA) with 103 glutamines forming protein aggregate, linked by GFP (green fluorescent protein) was transfected alone or together with DsRed1-C1-VRK1 or DsRed1-C1-VRK2, respectively linked by RFP (red fluorescent protein), in HEK293T cell lines to overexpress in a culture media containing DMEM/high glucose (Hyclone—cat. #SH30243.01), 10% (v/v) FBS (Hyclone) and 1% (v/v) penicillin-streptomycin (welgene, Korea) at 37° C., 5% $CO_2$ for 24 hours, and then, the aspect of aggregation of the overexpressed VRK1, VRK2, HTTQ103-GFP proteins were observed by fluorescent microscope (Carl Zeiss, Germany) and shown in FIG. 1a. For preparation of the DsRed1-C1-VRK1 or DsRed1-C1-VRK2, pDsRed1-C1 (BD Biosciences, San Jose, Calif.) was purchased and VRK1 (AB000449) and VRK2 (AB000450) were respectively cloned.

2) Experiment Results

As shown in FIG. 1a, the aspect of aggregation of each protein exhibited a dense shape and strong fluorescence intensity, and it was confirmed that the huntingtin protein exhibited increase in aggregate only when overexpressed together with VRK2. Specifically, as shown in the upper part of FIG. 1a, Htt-Q103 aggregate formation (green spot) was observed in VRK2-overexpressed cells, and to the contrary, as shown in the lower part of FIG. 1a, it was confirmed that in VRK1-overexpressed cells, Htt-Q103 protein is not aggregated and exists throughout the whole cell.

Based on the fluorescence microscope image of FIG. 1a, among the HttQ103-GFP expressed cells, the number of cells with aggregates was counted by visual inspection and quantified to show at the right side of FIG. 1a (n=3; vector represents a DsRed1-C1 mock vector used for transformation of VRK1 and VRK2 including Htt-exon1-GFP-pcDNA3.1 vector).

Therefore, it was confirmed that the Htt-Q103 protein aggregation induction and aggregate increase are specific to VRK2 protein, and are not related to VRK1.

1.2. Experiment of Huntingtin Protein Aggregation Induction in SK-N-BE(2)C Cell Line 1) Experiment Method Since it was confirmed that VRK2 has the function of huntingtin protein aggregation induction in Example 1.1, to test if the function is related to the enzyme activity of the VRK2, VRK2-KD(K61A) (a sequence wherein AAA (lysine) nucleotide sequence encoding 61st amino acid in the sequence of AB000450 is subjected to PCR-based SDM (Site Direct Mutagenesis) with GCA nucleotide sequence so as to coding alanine) wherein Lys which is 61st amino acid sequence in the amino acid sequence of VRK2 was point mutated with Ala to induce catalytic dead (KD) was used as control and compared with VRK2 (Accession no. AB000450).

And, to confirm if VRK2 functions for inducing protein aggregation in other kinds of cell lines, using the same method as Example 1.1, the aspects of huntingtin protein aggregation induction in human embryonic kidney cell line HEK293T and human neuroblastoma cell line SK-N-BE(2)C (ATCC (American Type Culture Collection), ATCC number: CRL-2268™) were compared and shown in FIG. 1b.

VRK2 and VRK2-KD(K61A) were cloned by amplifying each coding DNA sequence of the VRK2 and VRK2-KD (K61A) by PCR (1.95° C., 5 minutes, 2.95° C., 1 minute, 3.52° C., 1 minute, 4.72° C., 3 minutes 30 seconds, 5.72° C., 7 minutes, 6. 4° C., 10 minutes (2~4 were repeatedly conducted 35 cycles)) using cDNA obtained from HeLa cell line (Korean Cell Line Bank), forming sticky ends at pFlag- CMV2 vector (Sigma, St Louis, Mo.) and the amplified VRK2 and VRK2-KD(K61A) genes using Sal1 and BamH1 restriction enzyme (DCC-Bionet, Korea), and ligating them using T4 DNA ligase (Roche, Mannheim, Germany), to prepare pFlag-CMV2-VRK2 and pFlag-CMV2-VRK2-KD (K61A) plasmid DNA (see Kwon, S. Y., Y. J. Choi, T. H. Kang, K. H. Lee, S. S. Cha, G. H. Kim, H. S. Lee, K. T. Kim, and K. J. Kim., 2005. Highly efficient Protein expression and purification using bacterial hemoglobin fusion vector. Plasmid 53: 274-82). Primers used for the PCR are as follows.

<Used Primers>

```
VRK2 forward primer:
                                        (SEQ ID NO: 4)
5'-ACGCGTCGACATGCCACCAAAAAGAAATG-3'

VRK2 reverse primer:
                                        (SEQ ID NO: 5)
5'-AAGGATCCTCAGAGAAAAAATAAAGC-3'

K61A forward primer:
                                        (SEQ ID NO: 6)
5'-GCAAGACATGTAGTAGCAGTGGAATATCAAGAA-3'

K61A reverse primer:
                                        (SEQ ID NO: 7)
5'-TTCTTGATATTCCACTGCTACTACATGTCTTGC-3'
```

Figure 1B:
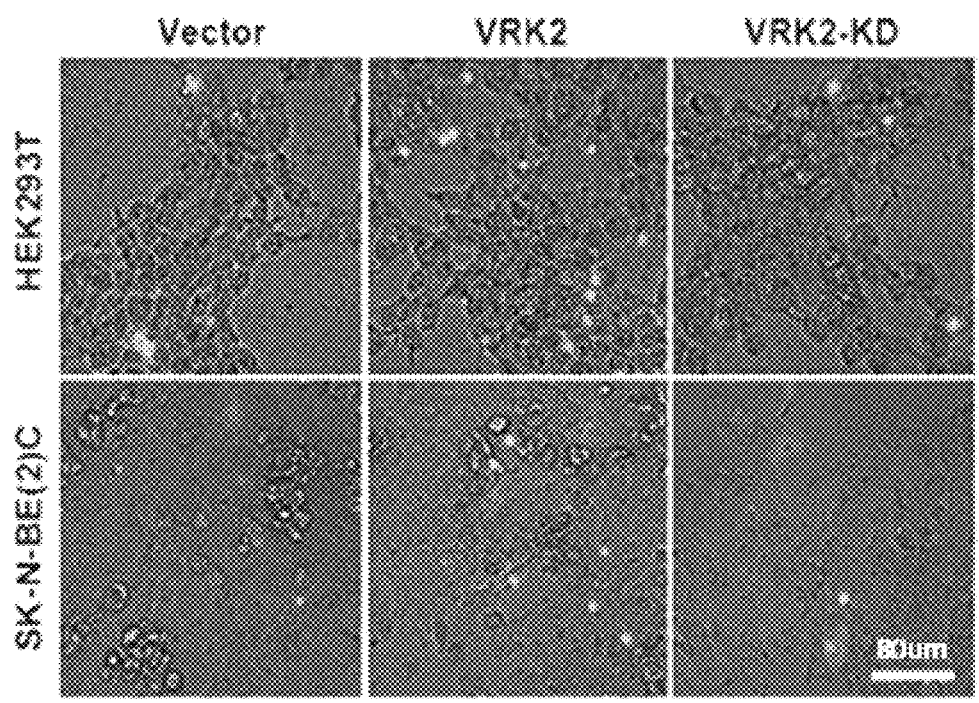

The prepared pFlag-CMV2-VRK2 and pFlag-CMV2-VRK2-KD (K61A) plasmid DNA were transformed into HEK293T cell line (Korean Cell Line Bank) and SK-N-BE (2) cell line (ATCC (American Type Culture Collection), ATCC number: CRL-2268™) using Htt-exon1-GFP-pcDNA3.1 vector (obtained from Judith Frydman, Stanford university, CA) and Metafectine (Biontex). And, per 60 mm culture dish, 6 µg of DNA and 18 µl of Metafectine (lipid) were respectively mixed with 300 µl of serum-free culture solution (DMEM (Hyclone)) and allowed to stand for 5 minutes, the two solutions were mixed and allowed to stand at room temperature for 30 minutes, and then, directly dripped to cells dropwise. 24 hours after transformation, protein aggregation in each cell was observed with fluorescence microscope (Carl Zeiss, Germany) and the results are shown in FIG. 1b.

Figure 1C:
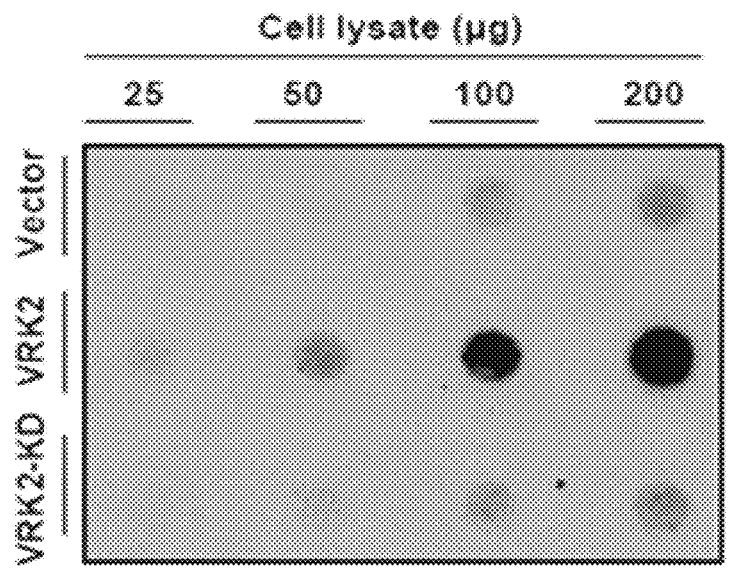

And, the amount of aggregated protein was examined by Filter trap assay (Nature Cell Biology, 2006, Vol. 8:1155-62) and shown in FIG. 1c. Specifically, cells (HEK293T) with each of the above proteins overexpressed were lysed in 0.5% (v/v) Triton X-100 PBS, dissolved in 1% (w/v) SDS-PBS again, and boiled at 95° C. for 5 minutes. And then, cell lysate was transferred to a nitrocellulose membrane having 0.2 µm pore using dot blotter (Bio-Rad, Hercules, Calif.), the membrane was coated with 5% (w/v) skim milk solution, and then, color formation was conducted using antibody to GFP protein (anti-green gluorescence protein (GFP)(B-2,sc-9996)(Santa Cruz, Calif.)) and secondary antibody (anti-mouse HRP-conjugated antibody (KPL)) to examine remaining aggregated protein.

2) Experiment Results

As shown in 1b, it was confirmed that in neuron SK-N-BE (2)C cell line as well as HEK293T cell line, when huntingtin protein is overexpressed with VRK2, huntingtin protein aggregation (green spot in FIG. 1b) is induced. And, the increase in Htt-exon1-GFP aggregate due to VRK2 protein as shown in FIG. 1a is insignificant when VRK2-KD without enzyme activity of VRK2 protein is overexpressed, thus confirming that the function of VRK2 for inducing huntingtin protein aggregation is dependent on VRK2 kinase activity.

This is explained in detail as follows.

Among the upper 3 images of FIG. 1b showing the experiment results in HEK293T cells, the first image from the left shows the results obtained by expression of Htt-exon1-GFP together with pFlag-CMV2 mock vector, which was used as a control. The aggregate indicated as a green spot means spontaneously induced aggregation of Htt-exon1-GFP protein. The second image shows the results obtained by expression of Htt-exon1-GFP protein together with catalytically active VRK2 protein, and it is confirmed that the number of aggregates indicated as a green spot significantly increases compared to the control. This suggests that aggregation of Htt-exon1-GFP is induced by VRK2. The third image shows the results obtained in cells where Htt-exon1-GFP protein and VRK2 protein without enzyme activity are expressed together, and it is confirmed that there is no significant difference in the number of aggregates indicated as a green spot compared to the control. Therefore, VRK2 enzymatic activity is important for induction of Htt-exon1-GFP aggregation.

The bottom 3 images of FIG. 1b are obtained in SK-N-BE (2)C cell, and the same appearance was shown as obtained in HEK293T cell. Thereby, it was confirmed that the increase in Htt-exon1-GFP aggregates by VRK2 occurs identically in neuron. Particularly, considering that most symptoms of neurodegenerative diseases occur in neuron, the experiment results suggest that symptoms of diseases may be induced by VRK2 identically.

And, as shown in FIG. 1c, it was also confirmed by the results of examining aggregated protein using Filter trap assay (Nature Cell Biology, 2006, Vol. 8:1155-62) that the amount of aggregated protein is dependent on kinase activity of VRK2. Specifically, in the case of a cell with overexpressed VRK2, due to protein aggregation, proteins that fail to pass the membrane and remain are observed.

Example 2

Measurement of Interaction Between VRK2 and Chaperonin

1) Experiment Method

Figure 2A:
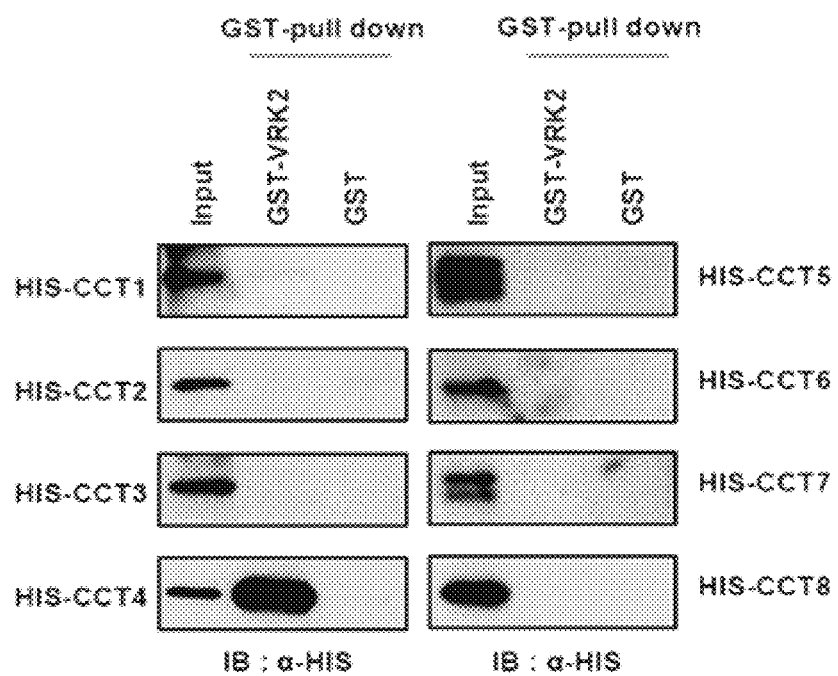
FIG. 2a to FIG. 2c show the results of measuring interactions of VRK2 and chaperonin according to Example 2.
Figure 2B:
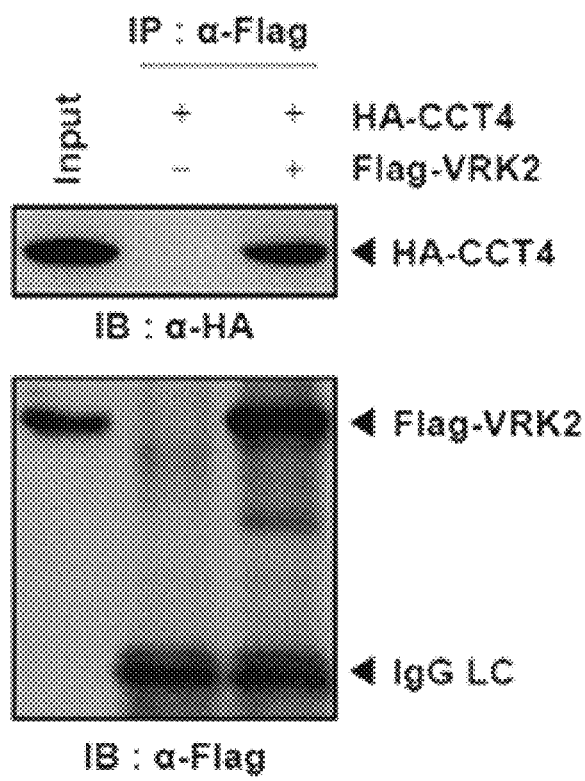

To examine interaction between VRK2 and chaperonin (TRiC/CCT), the degree of binding of VRK2 to each subunit (CCT1~8) of chaperonin was confirmed by GST pulldown assay and immunoprecipitation assay, and shown in FIG. 2a and FIG. 2b (see Kang, T. H. and K. T. Kim., 2006. Negative regulation of ERK activity by VRK3-mediated activation of VHR phosphatase. Nat Cell Biol 8: 863-9; 및 Kwon, S. Y., Y. J. Choi, T. H. Kang, K. H. Lee, S. S. Cha, G. H. Kim, H. S. Lee, K. T. Kim, and K. J. Kim., 2005. Highly efficient Protein expression and purification using bacterial hemoglobin fusion vector. Plasmid 53: 274-82, the references are incorporated herein by reference).

Materials used in this experiment were respectively GST antibody (SantaCruz), Glutathione sepharose 4B (GE healthcare), Flag antibody (Sigma), HA antibody (Roche), pFlag-CMV2-VRK2 prepared in Example 1.2, pGEX-4T3-VRK2, pProEx-HTa-CCTn (CCTn represents CCT1~CCT8; CCT1 (NM_013686), CCT2 (NM_007636), CCT3 (NM_009836), CCT4 (NM_009837), CCT5 (NM_007636), CCT6 (NM_009838), CCT7 (NM_007638), CCT8 (NM_009840)), and pcDNA3.1-HA-CCT4, and the pGEX-4T3-VRK2 and pProEx-HTa-CCTn were prepared by E. coli based cloning of VRK2 (AB000450) and CCTn respectively in a pGEX-4T-3 vector and a pProEx-HTa vector (Amersham, Piscataway, N.J.).

And, the pcDNA3.1-HA-CCT4 was prepared by E. coli based cloning of CCT4 in a vector synthesized by cutting pcDNA3.1 (Invitrogen, Carlsbad, Calif.) vector with Kpn1 and EcoR1 restriction enzyme (DCC-Bionet), synthesizing HA epitope (5'-ATGGCCTCCTACCCTTATGATGTGCCA-GATTATGCCTCTCCC-3': SEQ ID NO: 8) and cutting with the same restriction enzymes, and then, ligating with T4 DNA ligase (Roche). The restriction enzyme reaction was conducted at 37° C. for 16 hours, and ligation reaction was conducted at 16° C. for 16 hours.

Figure 2C:
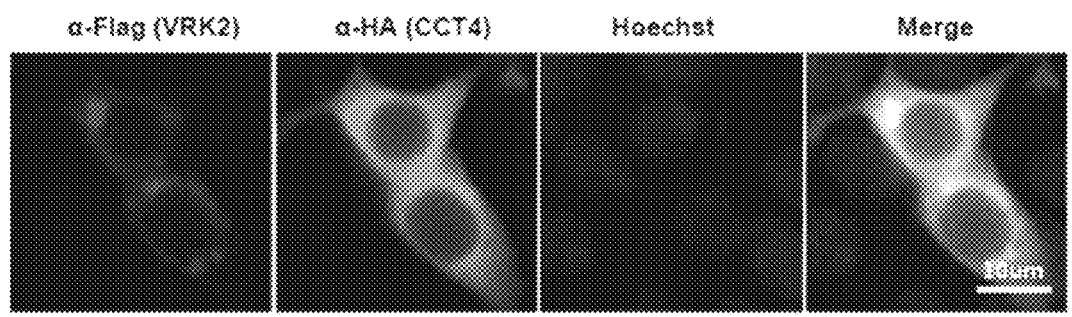

To confirm the location in the cell through the immunocytochemistry experiment, it was observed with fluorescent microscope (Carl Zeiss, Germany) and the results are shown in FIG. 2c.

Specifically, when HEK293T cells (Korean Cell Line Bank) grew approximately 50-60% on a coverslip, pFlag-CMV2-VRK2 and pcDNA3.1-HA-CCT4 were transformed by the same method as Example 1, and after 24 hours, the cells were fixed in 4% (w/v) paraformaldehyde for 15 minutes and washed with PBS three times. And then, Flag (sigma) and HA (Roche) antibodies were diluted to 1:1000 and incubated at 4° C. overnight, and then, washed with PBS three times. Alexa488 (Green, invitrogen), Alexa594 (Red, invitrogen) were diluted to 1:1000, incubated at room temperature for 1 hour, washed with PBS three times, and then, stained with Hoechst (5 μg/ml)(Sigma) at room temperature for 10 minutes, washed with PBS three times, and mounted on a slide glass to obtain an image with fluorescent microscope (Carl zeiss).

2) Experiment Results

As shown in FIG. 2a and FIG. 2b, it was confirmed that VRK2 and chaperonin, particularly CCT4 strongly bind in the experiment confirming the degree of binding between two molecules such as GST pulldown assay and immunoprecipitation (IP) assay.

FIG. 2a shows 8 images confirming chaperonin pulled down by VRK2, wherein in each image, the first from the left represents 5% of input, i.e., used chaperonin, the second represents the amount of chaperonin pulled down by VRK2, and the third is a control to the VRK2 protein (test group) and represents the amount of chaperonin pulled down by GST protein. The amount of chaperonin pulldown was confirmed using His Antibody (Santa Cruz) because it is tagged with 6× Histidine, and it was confirmed that among 8 subunits of chaperonin, particularly CCT4 was most strongly bound and pulled down.

The top image of FIG. 2b shows the amount of CCT4 protein pulled down by VRK2 in lysates. The first lane from the left represents 5% of input, i.e., used lysates during Immunoprecipitation. The second lane represents the amount of CCT4 protein pulled down by Flag antibody in the cells where only HA-tagged CCT4 is overexpressed. The third lane represents the amount of pulled down CCT4 protein when VRK2 was pulled down using Flag antibody in the cells where Flag-tagged VRK2 and HA-tagged CCT4 are overexpressed. The amount of CCT4 protein was confirmed using HA antibody. As shown in the top of FIG. 2b, chaperonin CCT4 was pulled down by VRK2, and thereby, it can be seen that VRK2 and CCT4 interact in the cells. And, from the bottom image, it was confirmed that the amount of VRK2 protein and the amount of antibody (light chain) used during Immunoprecipitation are identical.

And, the experiment confirming the location in the cells through immunocytochemistry also showed that two proteins occupy the same location and there is an opportunity to bind each other (FIG. 2c). In FIG. 2c, from the left, red represents the location of VRK2 protein, green represents the location of CCT4 protein, blue represents nucleus, and it is shown that VRK2 is distributed mainly in organelle around nucleus (ER and mitochondria), and CCT4 spreads over cytoplasm. As such, it is shown that VRK2 and CCT4 occupy the same space and they may interact. Thus, it was confirmed that the huntingtin protein aggregation inducing function of VRK2 suggested in Example 1 relates to the interaction between VRK2 and chaperonin (particularly, CCT4).

Example 3

Measurement of the Effect of VRK2 on the Amount and Stability of Chaperonin Protein 1) Experiment Method To measure the effect of huntingtin protein aggregation inducing function dependent on kinase activity of VRK2 on the amount and stability of chaperonin protein, the following experiment was conducted.

a. Preparation of GST-VRK2, GST-VRK2-KD Proteins

First, in order to control enzyme activity of VRK2, SDM (Site-directed mutagenesis) was conducted to construct a clone wherein 61st lysine reside is substituted with alanine. It is designated as VRK2-KD, and VRK2 and VRK2-KD were cloned into pGEX-4T-3 vector (Amersham, Piscataway, N.J.) to obtain GST-VRK2, GST-VRK2-KD proteins (Kang, T. H. and K. T. Kim., 2006. Negative regulation of ERK activity by VRK3-mediated activation of VHR phosphatase. Nat Cell Biol 8: 863-9). Enzyme inactivity of GST-VRK2-KD protein was confirmed by in vitro kinase assay. Specifically, 1 μg of protein, buffer (20 mM Tris-HCl pH7.5, 5 mM $MgCl_2$, 0.5 mM dithiothreitol, 150 mM KCl), and $^{32}P$-γ-ATP were mixed and cultured at 30° C. for 30 minutes, and then, SDS-PAGE was conducted, and image results were obtained using an x-ray film and shown in FIG. 3a.

b. Observation of Change in the Amount of CCT4 According to Enzyme Activity of VRK2

VRK2 gene with enzyme activity and VRK2-KD gene without enzyme activity were cloned into a pFlag-CMV2 vector by the same method as Example 1.2, and it was transformed into HEK293T cells using metafectene. After 24 hours, the cells were harvested from the culture dish using Trypsin (welgene), and the cells were centrifuged at 1500 rpm for 1 minute 30 seconds to collect. The collected cells were lysed at 4° C. for 30 minutes with RIPA buffer (50 mM Tris/HCl pH 8, 150 mM NaCl, 1% (v/v) NP-40, 0.5% (w/v) sodium Deoxycholate, 0.1% (w/v) SDS). And then, it was centrifuged at 15000 rpm for 30 minutes to obtain supernatant, which was quantified by Bradford assay, and SDS PAGE was conducted. And, to observe polyubiquitination of chaperonin to VRK2, 1 μg of CCT4 antibody (abcam) was mixed with the lysates, and immunoprecipitation was conducted. And then, they were transferred to a nitrocellulose membrane (Pall Corporation), the membrane was coated with 5% (w/v) skim milk, and Flag (Sigma), CCT4 (abcam), Ubiquitin (Santa Cruz) GAPDH (Santa Cruz) antibody were incubated at 4° C. overnight. And then, it was washed with washing buffer (0.05% (v/v) Tween 20 with TBS) three times for 10 minutes. And, HRP (Horseradish peroxidase)-bound secondary antibody (anti-mouse HRP-conjugated antibody (KPL)) was incubated at room temperature for 1 hour, and washed with washing buffer three times for 10 minutes. And, then, it was developed on an x-ray film through a color reaction using an ECL (enhanced chemiluminescence) solution, and the amount was confirmed and shown in FIG. 3b. The amount of VRK2 protein was confirmed by flag antibody (sigma), and GAPDH protein was used as a loading control.

c. Observation of Change in Stability of CCT4 According to Enzyme Activity of VRK2

Quantification was conducted through Bradford assay and SDS PAGE was performed by the same method as step b, except that VRK2- and VRK2-KD-overexpressed HEK2935 cells were treated with each 50 µg/ml of translation inhibitor cyclohexamide ((CHX), Calbiochem), and then, at 0, 4, 8 hours, the cells were harvested from the culture dish with Trypsin (welgene), and centrifuged at 1500 rpm for 1 minute 30 seconds to collect. And, immunoprecipitation was excluded, and the subsequent processes were conducted in the same manner as the step b, development was conducted on an x-ray film, and the results were shown in FIG. 3c. As such, since newly synthesized protein is inhibited by using translation inhibitor CHX, the stability of already existing protein may be confirmed.

d. Fractionation and Western Blotting Experiment

Extracts of VRKS-overexpressed HEK293T cells were fractionated using a FPLC device (Bio-Rad) equipped with Superdex200 gel-filtration column (GE healthcare). And then, western blotting was conducted for each fraction (see BMC Cell biol, 2002, 3; 30) (used material: CCT4 antibody (abcam), HSP70 antibody (santa cruz)).

2) Experiment Results

As shown in FIG. 3a to FIG. 3d, it was confirmed that the function of inducing huntingtin protein aggregation due to VRK2 enzyme activity as confirmed in Example 1 influences on the stability of chaperonin protein.

Figure 3A:
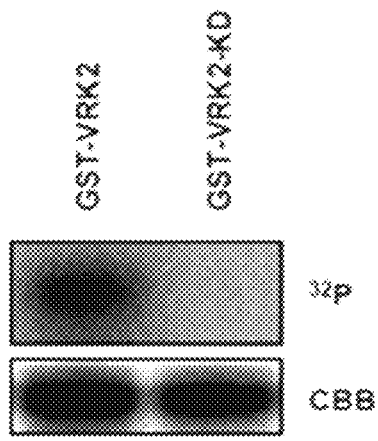
FIG. 3a to FIG. 3d show the results of measuring the effect of huntingtin protein aggregation induced by VRK2 on the stability of chaperonin protein according to Example 3.

First, referring to FIG. 3a, the top image shows autophosphorylation of VRK2, which means enzyme activity of kinase. To the contrary, it was confirmed that autophosphorylation disappeared in VRK2-KD. For reference, the bottom image shows that quantification of used protein by staining with coomassie Brilliant Blue G250 (Bio-Rad) is achieved well.

Figure 3B:
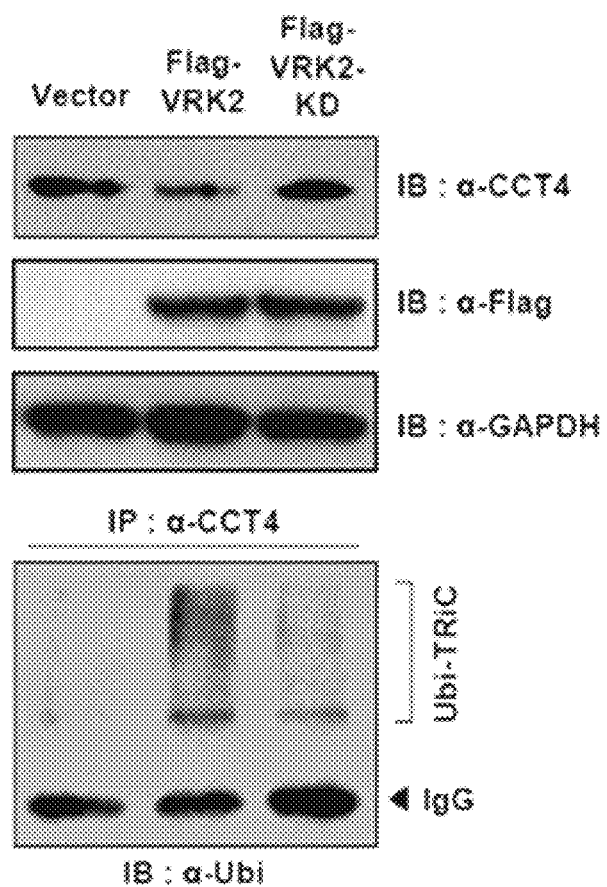

In FIG. 3b, 3 images of the top represents the amount of each protein in the cells, and the bottom image shows distribution of ubiquitin protein tagged at CCT4. As shown in the bottom image, if VRK2 enzyme activity exists, label of polyubiquitination, which is a protein degradation signal, increases in chaperonin, and this phenomenon decreases a lot when VRK2 enzyme activity disappears. Similarly, it was confirmed in the top images that the amount of chaperonin (CCT4) in the cells decreases when protein with VRK2 enzyme activity is overexpressed, and thereby, it can be seen that VRK2 enzyme activity is important for decrease in the amount of chaperonin.

Figure 3C:
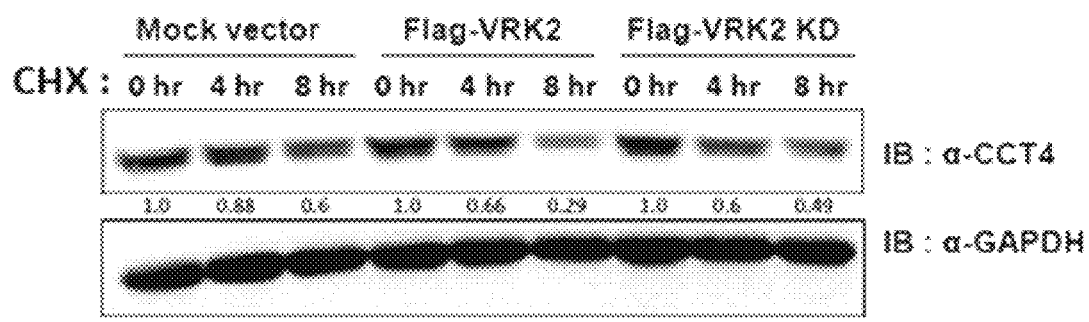

Meanwhile, referring to FIG. 3c showing the results of treating translation inhibitor CHX, the top image represents the lifespan of chaperonin in VRK2-VRK2-KD-overexpressed cells, and the bottom image represents the amount of GAPDH protein as a loading control. It was confirmed that the lifespan of chaperonin decreases dependently on the enzyme activity of VRK2 protein, which coincides with the results shown in FIG. 3b.

Specifically, if the amount of protein with VRK2 enzyme activity is increased, the amount of chaperonin (CCT4) labeled with protein degradation signal polyubiquitination increases, and thereby, both the amount and stability of chaperonin (CCT4) decrease (FIG. 3b and FIG. 3c).

Figure 3D:
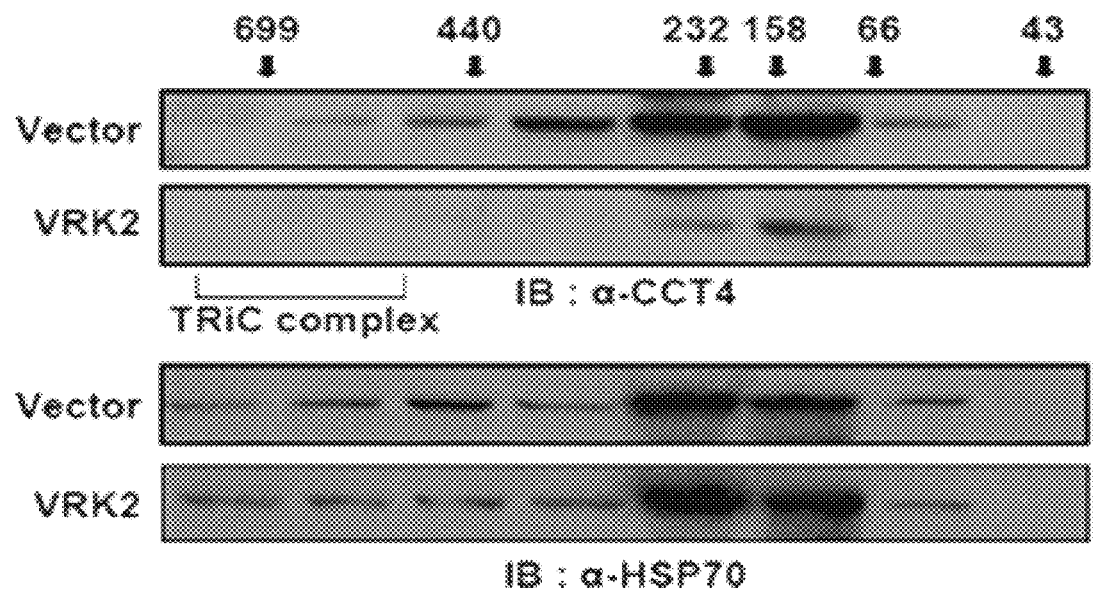

Referring to FIG. 3d, it is shown that the size of protein decreases from the left to the right. Since chaperonin includes 2 bound complexes each consisting of 8 subunits to act, the complex size is very large. However, when VRK2 protein is overexpressed, it is confirmed that the amount of chaperonin decreases in the fraction where the complex appears. This means that the formation of the complex is inhibited due to decrease in the amount of CCT4 protein by VRK2. Namely, it is suggested that as the amount of CCT4, one of subunits of chaperonin, decreases by VRK2, chaperonin fails to form a complex and the amount of monomer comparatively increases, and thus, the function of chaperonin is lowered (FIG. 3d).

Example 4

Identification of Biofactor Relating to the Effect of VRK2 on the Stability of Chaperonin Protein 1) Experiment Method To identify biofactors relating to decrease in the stability of chaperonin protein due to VRK2 as confirmed in Example 3, the following experiment was conducted. The sequence of siRNA to each protein used in this experiment and the following Example 5 is as follows.

```
siRNA to VRK2 (siVRK2)
                                        (SEQ ID NO: 1)
GCAAGGUUCUGGAUGAUAUUU (D-004684-06, Dharmacon)

siRNA to COP1 (siCOP1)
                                        (SEQ ID NO: 2)
GAAAUGACCUGCAAUUCGA (D-007049-01, Dharmacon)

siRNA to RBX1 (siRBX1)
                                        (SEQ ID NO: 3)
GACUUUCCCUGCUGUUACCUAA (Dharmacon)
``` a. Confirmation of the Role of COP1 for Control of the Amount of Chaperonin by VRK2

To confirm whether the role of COP1, one of ubiquitin ligase, influences on the control of the amount of chaperonin by VRK2, pFlag-CMV-VRK2 used in Example 1.2 and siRNA to COP1 were transformed into HEK293T cell line (Korean Cell Line Bank) using microporator (invitrogen). Specifically, 2 µg of pFlag-CMV-VRK2 and 2 µl of siRNA (siCOP1, D-007049-01) (20 µM) were mixed with $1.0 \times 10^6$ cells, and electroporation was conducted.

Figure 4A:
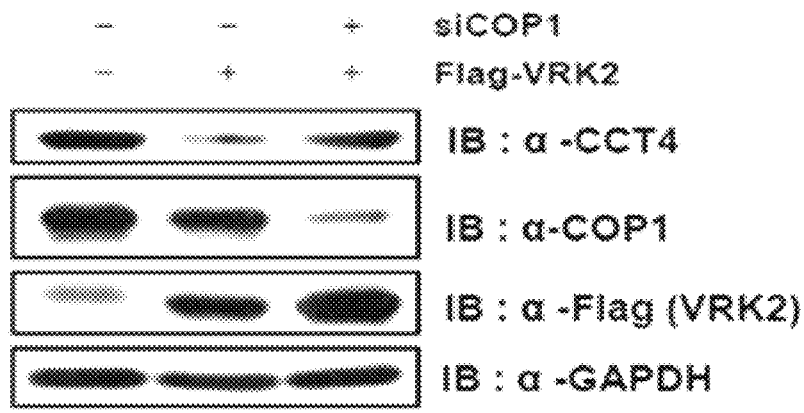
FIG. 4a to FIG. 4c show the results of investigating biofactor involved in huntingtin protein aggregation induction of VRK2 according to Example 4.
Figure 4B:
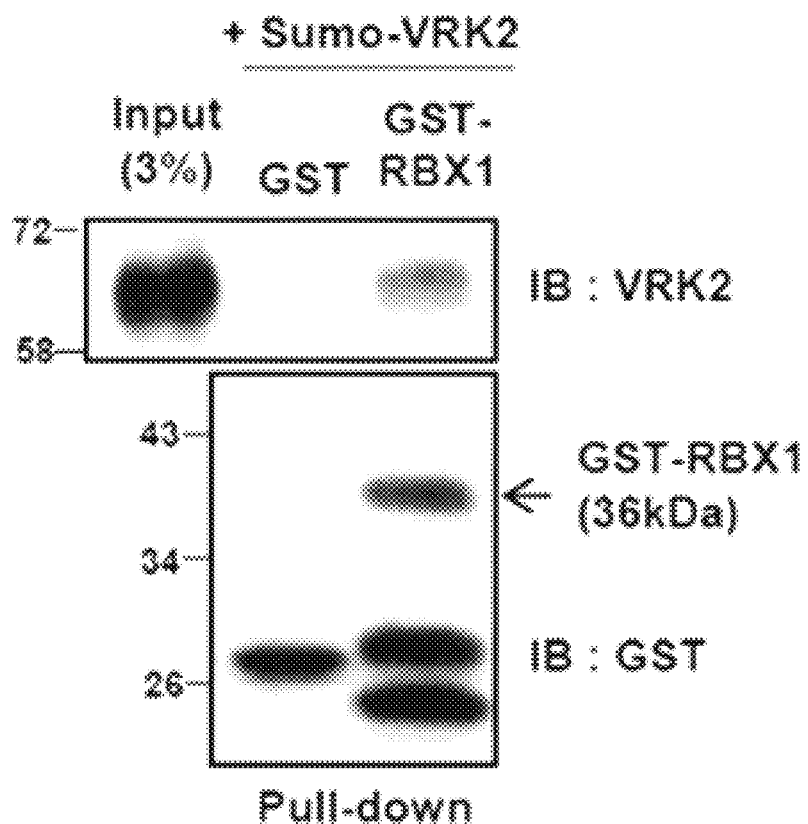

24 hours after transfection through electroporation, the cells were harvested from the culture dish using Trypsin (welgene) and centrifuged at 1500 rpm for 1 minute 30 seconds. Subsequent processes of quantifying through Bradford assay, conducting SDS PAGE and developing on an x-ray film through a color reaction using an ECL (enhanced chemiluminescence) solution to confirm the amount were conducted in the same manner as Example 3.1) b, and the results are shown in FIG. 4a. And then, GST-pulldown assay was performed using GST-tagged RBX1 (Accession no. AF140598) and SUMO-tagged VRK2, and the results are shown in FIG. 4b (See Kang, T. H. and K. T. Kim., 2006. Negative regulation of ERK activity by VRK3-mediated activation of VHR phosphatase. Nat Cell Biol 8: 863-9).

b. Confirmation of the Role of COP1 for the Reduced Stability of Chaperonin by VRK2 siRNA to COP1 and VRK2 were transfected into HeLa cell line (Korean Cell Line Bank) using microporator (invitrogen).

Specifically, 2 µl of siRNA (20 µM) was mixed with $1.0 \times 10^6$ cells, and electroporation was conducted. 24 hours after transfection through electroporation, they were treated with 50 µg/ml of translation inhibitor CHX, and after 0, 4, 8, 12 hours, the cells were harvested from the culture dish using Trypsin (welgene) and centrifuged at 1500 rpm for 1 minute 30 seconds to collect.

Figure 4C:
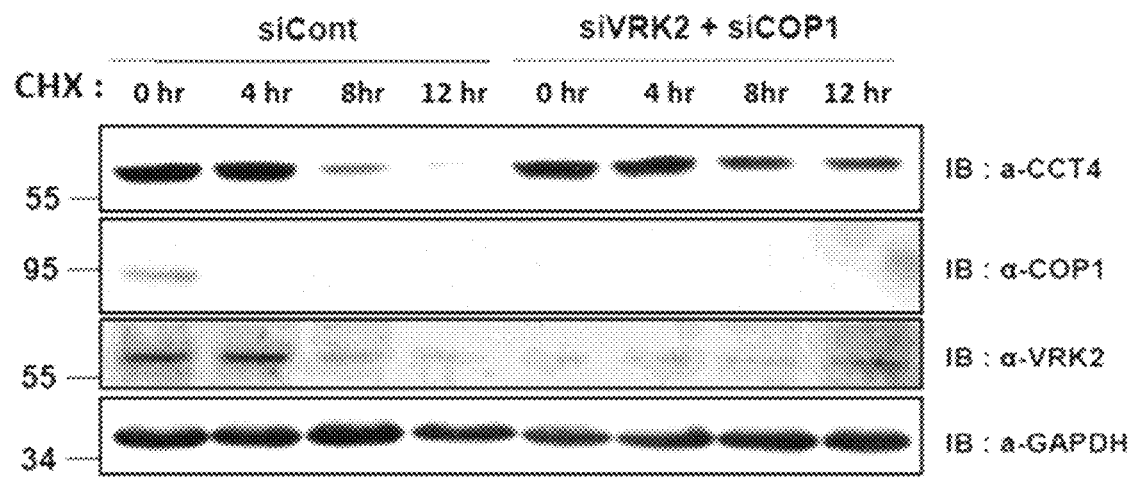

Subsequent processes of quantifying through Bradford assay, conducting SDS PAGE, and developing on an x-ray film through a color reaction using ECL (enhanced chemiluminescence) solution to confirm the amount were conducted in the same manner as Example 3.1) b, and the result are shown in FIG. 4c.

2) Experiment Results

As shown in FIGS. 4a to 4c, it was confirmed that ubiquitin ligase COP1 (Accession BC094728) is involved in chaperonin degradation mechanism.

Each image of FIG. 4a shows the amount of protein in the cells when the amount of VRK2 and COP1 were controlled. As confirmed in FIG. 3b, the amount of chaperonin decreases when the amount of VRK2 is increased, and even if the amount of VRK2 is increased, when the amount of ubiquitin ligase COP1 is decreased, the amount of chaperonin is not decreased. Thereby, it can be seen that COP1 ubiquitin ligase acts on chaperonin degradation mechanism on which VRK2 acts. Namely, it was confirmed that if the expression amount of COP1 is decreased, the effect of VRK2 on decrease in the amount of CCT4 is inhibited (FIG. 4a). Referring to FIG. 4b, it was confirmed that RBX1, which is one of the constitutional elements of COP1 ubiquitin ligase, and VRK2 are pulled down together during GST-pulldown assay, and thus, it was confirmed that VRK2 interacts with RBX1 (Accession no. AF140598), one of the constitutional elements of COP1 ubiquitin ligase.

Referring to FIG. 4c, it was confirmed that when the expression amounts of both VRK2 and COP1, which are considered to play an important role in chaperonin degradation mechanism, are decreased, the stability of chaperonin protein is increased compared to control. Therefore, it can be seen that VRK2 kinase and COP1 ubiquitin ligase act on the chaperonin degradation process.

As explained, it was confirmed that biofactor relating to decrease in the stability of chaperonin protein by VRK2 as confirmed in Example 3 is COP1, particularly RBX1, which is the constitutional element of the complex of COP1, and thus, it was confirmed that if the expression of COP1 is inhibited by siRNA to COP1, the effect of VRK2 on the decrease of the amount and/or stability of chaperonin protein may be inhibited.

Example 5

Figure 5A:
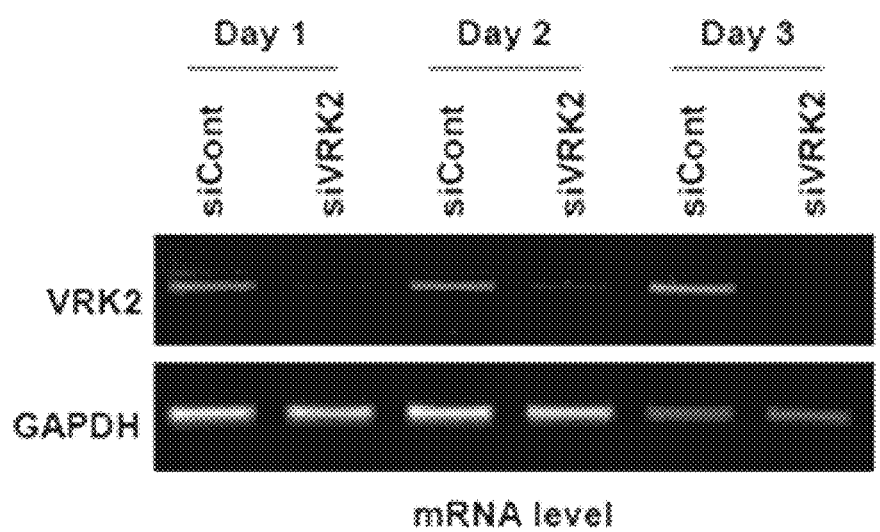
FIG. 5a to FIG. 5c show the effect of decrease in the expression amount of VRK2 on chaperonin (inhibition of huntingtin protein aggregation) according to Example 5.
Figure 5B:
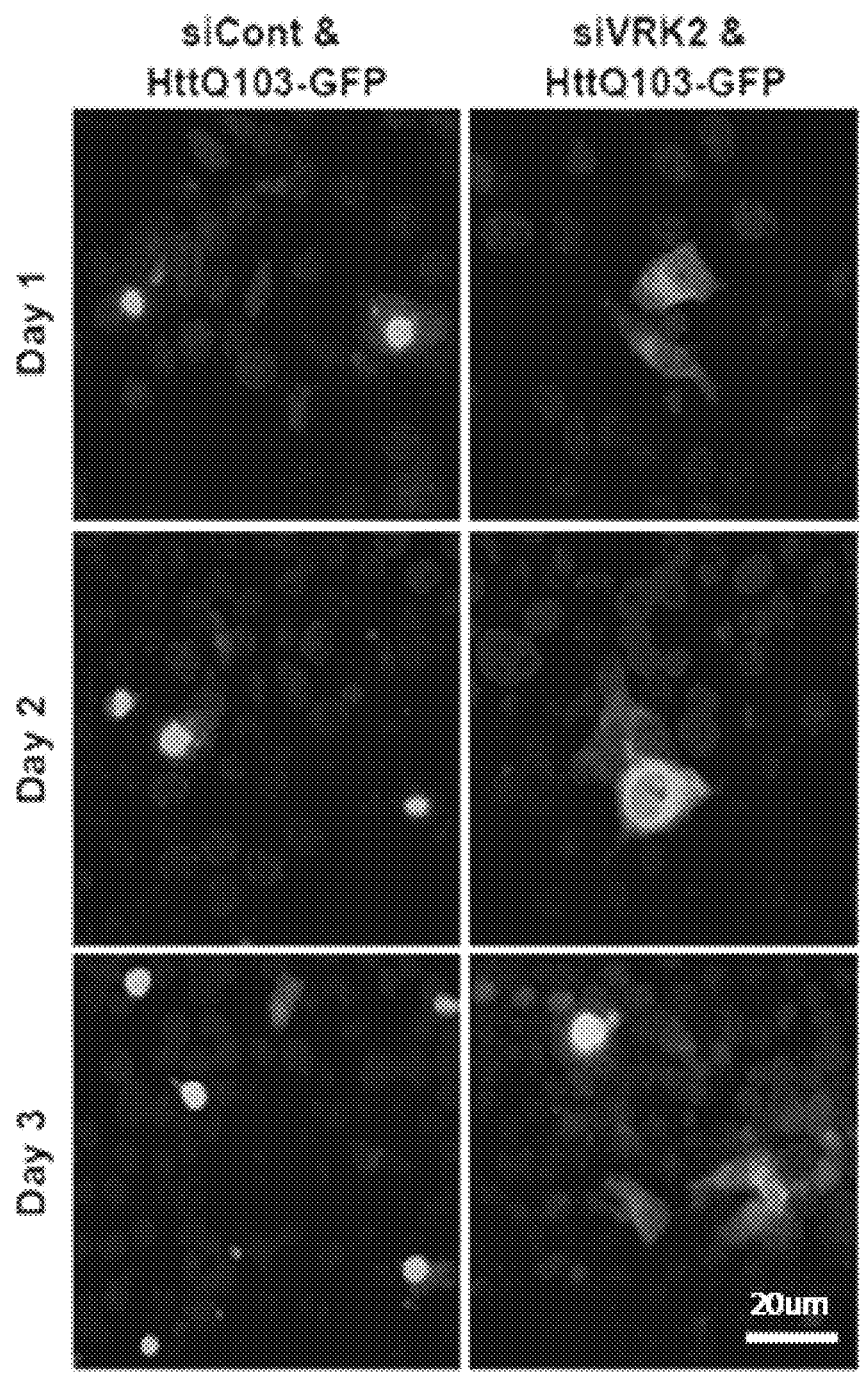
Figure 5C:
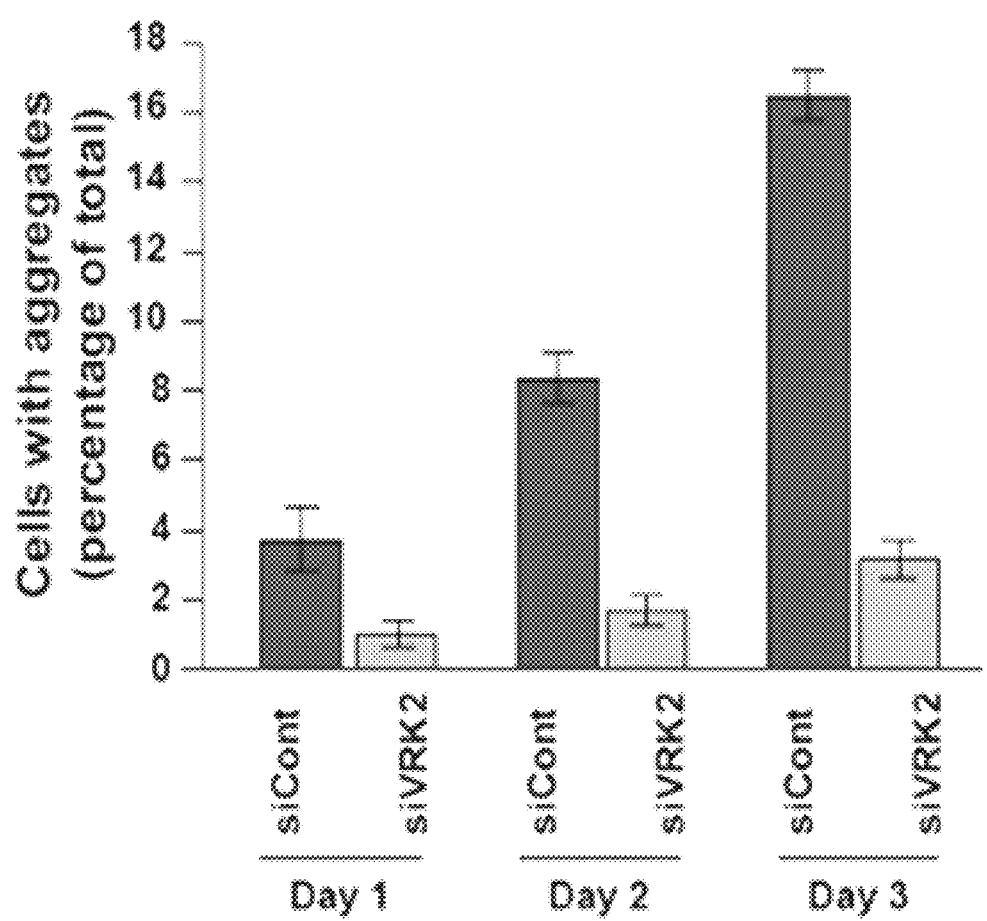

Measurement of the Effect of Decrease in the Expression Amount of VRK2 on Chaperonin 1) Experiment Method The effect of decrease in the expression amount of VRK2 on chaperonin, i.e., change in the amount of huntingtin protein aggregate was measured and shown in FIG. 5a to FIG. 5c.

To achieve this, overexpression of huntingtin protein was induced in HeLa cell line (Korean Cell Line Bank) by the same method as Example 1. And then, to remove VRK2 protein in the cells, siRNA targeting mRNA of VRK2 (sdiVRK2) and control siRNA (siCont) were obtained from Dharmacon (USA), and used for efficiency verification and decrease in the expression amount of VRK2 in the cells.

Specifically, on a 24 wells plate, 2.5 µl of Dharma FECT1 (siRNA transfection reagent) and 2.5 µl of 5 µM siVRK2 were respectively mixed with 47.5 µl of serum-free culture solution (DMEM/high glucose (Hyclone)), and after 5 minutes, the two solutions were mixed, allowed to stand at room temperature for 20 minutes, and directly dripped to cell dropwise to transfect siVRK2 (D-004684-06, Dharmacon). After 1, 2, 3 days, the cells were dripped on trypsin (welgene) and centrifuged at 1500 rpm for 1 minute 30 seconds to obtain cells. And then, the total RNA was extracted using TRI reagent (Molecular Research Center) and cDNA was obtained using reverse transcriptase (Promega) (see Nucleic Acid Res, 2010, 38(20): 7068-78).

The obtained cDNA and VRK2 (Accession AB000450), and GAPDH (Accession NM_002046) primers (10 pM) 1 µl were mixed and PCR was conducted.

<Used Primer>

```
VRK2 RT primer
Forward primer:
                                      (SEQ ID NO: 9)
5'-TTTAGCATATGATGAAAAGCCAAACTATCA-3'

Reverse primer:
                                     (SEQ ID NO: 10)
5'-TGAGACTCTTGATATTTCTGTCTTCTCCTT-3'

GAPDH RT primer
Forward primer:
                                     (SEQ ID NO: 11)
5'-CTTTGGTATCGTGGAAGGACTCATGACCAC-3', Reverse primer:
                                     (SEQ ID NO: 12)
5'-CCACCACTGACACGTTGGCAGTGGGGACAC-3'
```

PCR condition: 1.95° C. 10 minutes, 2.95° C. 15 seconds, 3.60° C. 1 minutes, 2 to 3 steps were conducted 40 cycles.

PCR product was electrophoresed in 1.5% (w/v) agarose gel, and then, observed by UV transmilluminator (UVP), and the results are shown in FIG. 5a.

Next, when HeLa cell line grows approximately 5-60% on a coverslip, siRNA (siVRK2, siCont) and Htt-exon1-GFP (HttQ103-GFP) of Example 1 were transfected into HeLa cell line using the above explained transfection method. After 1, 2, 3 days, the cells were fixed in 4% (w/v) paraformaldehyde for 15 minutes, and washed with PBS three times. And then, they were stained with Hoechst (5 µg/ml)(Sigma) at room temperature for 10 minutes, washed with PBS three times, mounted on a slide glass, and image was obtained with fluorescent microscope (Carl zeiss) (FIG. 5b), and the obtained results were quantified and shown in FIG. 5c.

2) Experiment Results

As shown in FIG. 5, it was confirmed that when the expression amount of VRK2, clarified as chaperonin modulator in Example 2, is lowered by using siRNA, the function of chaperonin is improved and thus, the amount of huntingtin protein aggregate is decreased.

As shown in FIG. 5a, siVRK2 (Dharmacon, USA) targeting mRNA of VRK2 was used to remove VRK2 protein in the cells, and as the result, expression of VRK2 was not detected.

And, as shown in FIG. 5b, as the results of observing huntingtin protein aggregation in test group (cells wherein VRK2 protein formation was inhibited using siVRK2) and control (cells wherein VRK2 protein formation was not inhibited) with fluorescent microscope, in the cells wherein VRK2 protein formation was inhibited, huntingtin protein was not aggregated and spread over the whole cells, and thus, it was confirmed that huntingtin protein aggregation decreased a lot.

More specifically, referring to FIG. 5c which shows the number of cells with aggregates as a graph, at 1 day, percent (%) of cells with aggregates to total cells was about 4% for control, and only about 1% for test group, and thus, the rate of cells with aggregates is about 4 times higher in control, and thus, it can be seen that huntingtin protein aggregation significantly decreases as VRK2 protein decreases. And, at 3 day, test group shows the rate of cells with aggregates below about 4%, which was the rate detected in control group at 1 day, while control shows the rate of about 17%, which is about 4 times greater, and thus, it was confirmed that difference in the effect became larger over time.

As explained, it can be seen that VKR2 and/or COP1 (particularly, RBX1) act as an effective negative modulator of chaperonin which is involved in protein aggregation inducing neurodegerative diseases. Therefore, the present invention may be very useful for treatment or prevention of neurodegenerative diseases.

The invention claimed is:

1. A method of screening for a CCT4 modulator, the method comprising
   1) preparing a candidate material and VRK2;
   2) measuring an expression amount or a kinase activity of the VRK2;
   3) treating the VRK2 with the candidate material and measuring a change in the expression amount or the kinase activity of the VRK2; and
   4) determining the candidate material as the CCT4 modulator by comparing the expression amount or the kinase activity of VRK2 between the treated and untreated groups.

2. The method according to claim 1, wherein the CCT4 modulator increases an expression amount or a stability of CCT4 protein, and
   the step 4) is performed by identifying the candidate material as a material that increases the expression amount or the stability of CCT4 protein if the expression amount or the kinase activity of VRK2 is decreased compared to untreated group.

3. The method according to claim 1, wherein the CCT4 modulator decreases an expression amount or a stability of CCT4 protein, and
   the step 4) is performed by identifying the candidate material as a material that decreases the expression amount or stability of CCT4 protein if the expression amount or the kinase activity of VRK2 is increased compared to untreated group.

* * * * *